United States Patent [19]

Macur

[11] Patent Number: 5,431,166
[45] Date of Patent: Jul. 11, 1995

[54] LOW PROFILE MEDICAL ELECTRODE

[75] Inventor: Robert A. Macur, Mukwonago, Wis.

[73] Assignee: Ludlow Corporation, Exeter, N.H.

[21] Appl. No.: 7,446

[22] Filed: Jan. 22, 1993

[51] Int. Cl.$^6$ .................. A61B 5/0402; A61N 1/04
[52] U.S. Cl. ................... 128/640; 607/149; 607/152
[58] Field of Search ............ 128/639, 640; 607/149, 607/152, 153

[56] References Cited

U.S. PATENT DOCUMENTS

| | | | |
|---|---|---|---|
| 2,943,628 | 7/1960 | Howell | 128/418 |
| 3,085,577 | 4/1963 | Berman et al. | 128/418 |
| 3,606,881 | 9/1971 | Woodson | 128/2.06 E |
| 3,741,219 | 6/1973 | Sessions | 607/153 |
| 3,828,766 | 8/1974 | Krasnow | 128/417 |
| 3,998,215 | 12/1976 | Anderson et al. | 128/2.06 E |
| 4,063,352 | 12/1977 | Bevilacqua | 29/630 R |
| 4,094,822 | 6/1978 | Kater | 128/640 X |
| 4,166,453 | 9/1979 | McClelland | 128/639 |
| 4,522,211 | 6/1985 | Bare et al. | 128/640 |
| 4,570,637 | 2/1986 | Gomes et al. | 128/641 |
| 4,679,563 | 7/1987 | Wada et al. | 128/640 |
| 5,133,356 | 7/1992 | Bryan et al. | 128/640 |
| 5,168,875 | 12/1992 | Mitchiner | 128/640 |
| 5,215,087 | 6/1993 | Anderson et al. | 128/640 |

Primary Examiner—Lee S. Cohen
Attorney, Agent, or Firm—Richard H. Kosakowski; Holland & Associates

[57] ABSTRACT

An electrode having an extremely low profile and suitable for disposable use includes a base sheet constructed of a flexible conductive polymer. A tab is laminated to the top of the base sheet to form a pocket between the tab and the base sheet extending along the base sheet for receiving a hook connector. The hook connector has a bill and shank joined by a bend, the bill fitting between the pocket and the shank lying on top of the tab when the bill is so engaged to allow a low profile connection to the electrode. The elimination of rigid parts from the electrode improves its comfort and functionality.

11 Claims, 3 Drawing Sheets

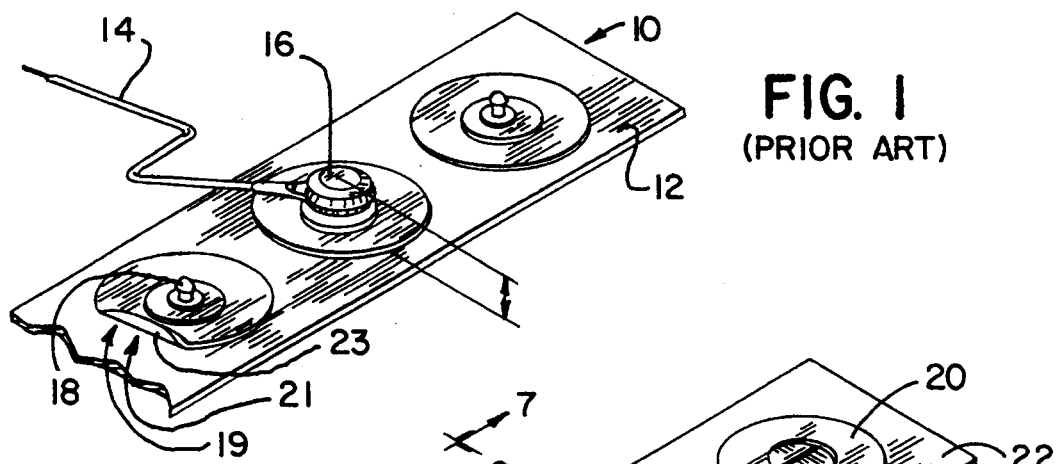
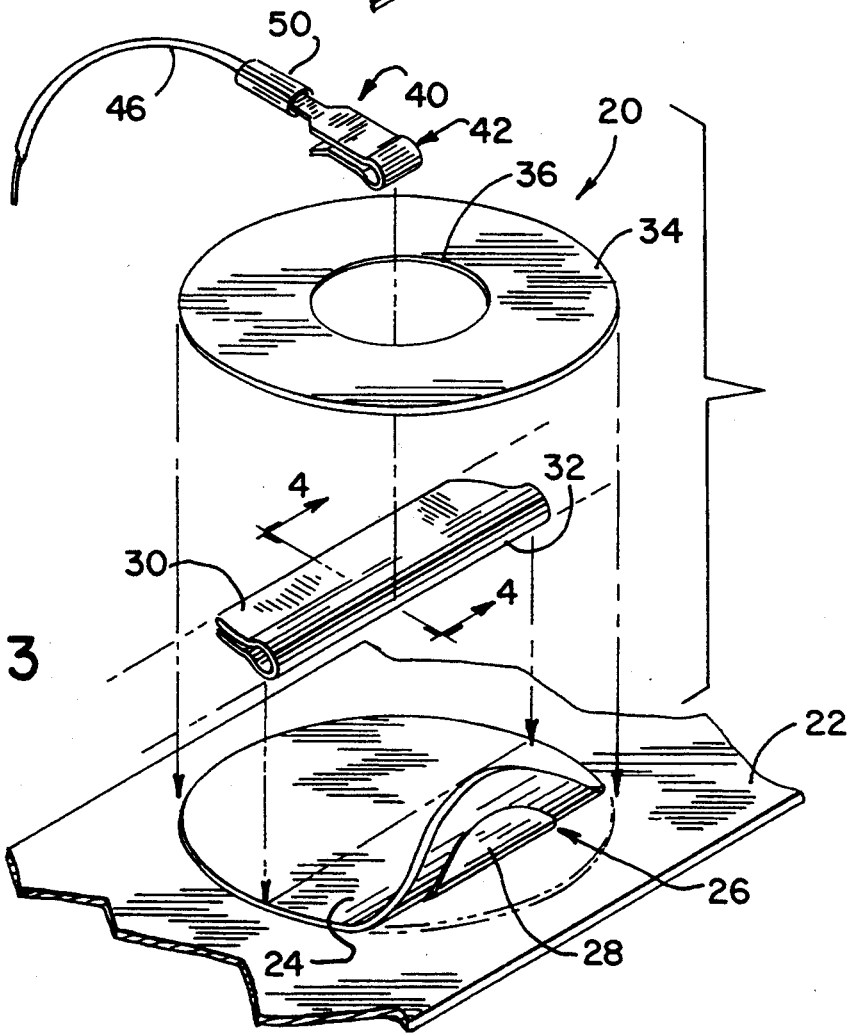

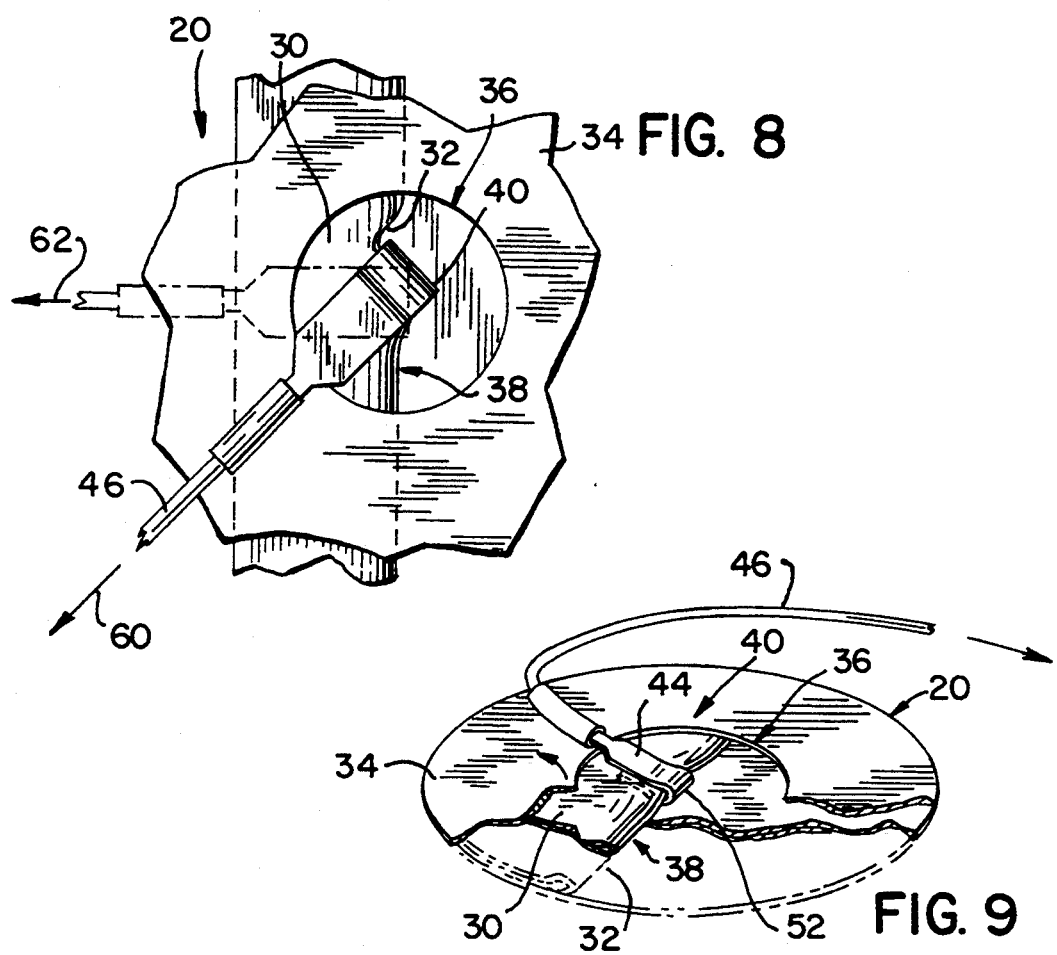
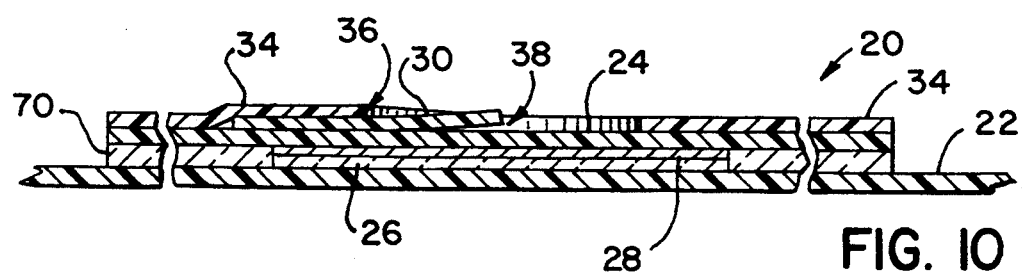
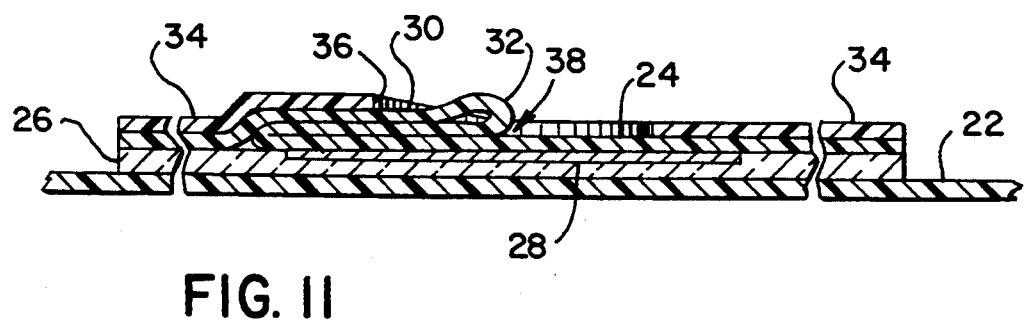

//  5,431,166

LOW PROFILE MEDICAL ELECTRODE

FIELD OF THE INVENTION

This application relates to medical electrodes and in particular to an improved method and apparatus for attaching such electrodes to monitoring leads.

BACKGROUND OF THE INVENTION

Medical electrodes provide an electrical interface between a patient and monitoring equipment, e.g., an electrocardiograph device, or between a patient and stimulating equipment, e.g. defibrillation equipment.

Interest in reducing the transmission of communicable diseases in the hospital environment has increased the demand for the development of disposable medical equipment including electrodes. Referring to FIG. 1, a typical disposable electrode 10, meeting this demand, is packaged attached to a card 12 from which it may be removed for use.

A non-disposable lead wire 14 connects the electrode 10 to external monitoring or stimulating equipment (not shown). The lead wire 14 and the electrode 10 are joined at the interface of female connector 16, molded to one end of the lead wire 14, and male connector 18 attached to each electrode 10. The male connector 18 may be the boss of a low cost "snap" type connector, in keeping with the disposable nature of the electrode 10.

The contact resistance between the electrode 10 and the patient's skin may be reduced by the use of an electrolyte 19 between the skin-contacting surface of the electrode 10 and the patient's skin. An electrochemically active material 21 is also frequently incorporated into the skin-contacting surface of the electrode 10 to further enhance the electrically conducting characteristics of the electrode. This electrochemically active material may be a metal and its salt, such as silver and silver chloride.

The electrode 10 also may include adhesive 23 on its skin-contacting surface to physically anchor the electrode 10 against forces from the lead wire 14. The central positioning of the connector 18 within a ring of circumferential adhesive 23 provides this design with good resistance to peeling away with lateral force on the lead wire 14.

Although inexpensive, connectors 16 and 18 have a number of drawbacks. First, the connection force needed to separate connectors 16 and 18 is substantial and, therefore, connector 16 must be of sufficient size to enable medical professionals to grasp it firmly for removal. During connection of connectors 16 and 18, the downward engaging force applied to connector 16 may be uncomfortable to patients sensitive to compression; for example, those recovering from thoracic surgery. Further, often, it is desirable to leave the electrode 10 in place for a length of time to ensure the reproducibility of the measurements made. Male connector 18 projects a significant distance upward from the surface of the electrode 10 and can be uncomfortable when it is compressed by a mattress or other support against the patient. This problem is compounded when the female connector 16 is connected to male connector 18. For ambulatory patients, the projection of connectors 16 and 18 may interfere with ordinary clothing.

Connectors 16 and 18 include plated metallic material and, when x-rays are taken, produce an artifact in the x-ray image. This metallic portion is subject to undesirable corrosion when electrodes 10 are packaged in a "pre-gelled" state (with the electrolyte 19 applied) in hermetic packages.

It has also been determined that the snap system of connectors 16 and 18, modeled after a mechanical closure for clothing, does not provide a wiping action during connection and disconnection, and therefore is subject to developing detrimental high contact resistance.

SUMMARY OF THE INVENTION

The present invention provides a low cost flexible electrode, resistant to the peeling away with force on the monitoring lead, but that avoids the problems of the prior art connector system.

Specifically, the electrode employs a flexible base sheet having a first side to be placed next to the skin of the patient. A flexible conductive tab is placed on the second side, opposite the first side of the base sheet, so as to form a pocket between the second side of the base sheet and the bottom surface of the tab. The pocket receives a specially designed electrical connector which establishes electrical contact between the connector and the electrode.

It is the first object of the invention to eliminate the rigid snap-type connector of the prior art and to create a medical electrode that is flexible over its entire area and thus more comfortable. Prior to its connection to the monitoring lead, all portions of the electrode are yielding and may conform to the patient's skin. The unconnected electrode offer no points of pressure when compressed against the skin by clothing or a mattress.

It is another object of the invention to create a medical electrode that may be left in place during radiographic procedures. Because the dense portions of the snap-type connector have been eliminated, the electrode of the present invention offers virtually no attenuation to x-rays and the small amount of attenuation that is produced is extremely uniform over the electrode surface.

It is yet another object of the invention to provide a pre-gelled electrolyte that has improved shelf life. Elimination of metallic elements in the construction of the electrode allows the electrode to be stored with electrolyte applied to its active surface in a closed pouch for an indefinite period of time. Corrosion of metallic snap parts in the humid environment of the pouch are eliminated.

An electrical connector for connecting the electrode of the present invention with monitoring leads may be a simple hook having a shank extending along a first axis to a second end to join with a bill attached to the second end of the shank at a bend. The bill returns substantially along the first axis. The bill is sized to fit within the pocket of the tab with the tab between the bill and shank.

Thus, it is another object of the invention to provide an electrode connector that provides good contact with the electrode; ease of insertion with low insertion force; and simple design for complete cleaning. Insertion of the bill within the pocket provides a wiping action which promotes good contact to the pocket. The contacting area of the bill and shank may be increased arbitrarily to the limits of the pocket size to provide the necessary area of contact. The pocket may be larger than the bill to make it easy to locate the pocket and insert the bill. The connector's simple design with no closed internal recesses allows it to be readily cleaned.

It is yet another object of the invention to provide a connector that has an extremely low profile when attached to the electrode. When inserted in the pocket, the connector lies flat along the plane of the electrode and thus does not substantially increase the profile of the electrode.

The tab to which the connector is attached may be a strip of flexible conductive material having a folded edge. The bend of the electrical connector, between the shank and bill, may form an expanded area allowing this folded edge to expand when the electrical connector is in position, thereby resisting disengagement of the electrical connector from the pocket. The electrical connector may include barbs directed toward the bill to further resist disengagement of the electrical connector from the tab. Alternatively, the bill may include a detent surface spaced from the shank so that insertion of the tab between the bill and shank causes the outward flexure of the bill and shank insuring compressive connection to the tab. The electrode may have an adhesive surface and the pocket may be centered within that surface so that force exerted on the pocket by the connector is spread evenly to the area of the skin through the adhesive, resisting peel away of the electrode.

Thus, it is another object of the invention to provide a connector system that resists disengagement of the connector from the electrode and further resists peeling of the electrode away from the patient, with tension on the lead.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, reference must be made, therefore, to the claims herein for interpreting the scope of the invention.

BRIEF DESCRIPTION OF THE DRAWINGS

FIG. 1 is a perspective view of a prior art card of electrodes, as discussed above in the Background of the Invention, showing the connector system employed and the high profile of these electrodes;

FIG. 2 is a figure similar to that of FIG. 1 showing the electrodes and connector of the present invention and the reduced profile height of the connector and electrode when assembled;

FIG. 3 is an exploded perspective view of one electrode of FIG. 2 showing construction of a pocket in the electrode for connection to the connector by use of a folded strip sandwiched between a base layer and an annular retainer sheet;

FIG. 8 is a planar view of the electrode of FIG. 2 showing deformation of the pocket wall with lateral force on the connector, such deformation serving to retain the connector in engagement with the electrode during such forces.

FIG. 9 is a perspective cutaway view of the electrode of FIG. 2 showing motion of the connector with respect to the electrode with backward force on the lead wire showing the hooking action of the electrical connector resisting disengagement from the electrode;

FIG. 10 is a view similar to that of FIG. 4 showing construction of the pocket of the electrode from a single unfolded sheet of conductive material; and FIG. 11 is a figure similar to that of FIGS. 4 and 10 showing a third embodiment of the invention where the pocket is formed from a fold in the base sheet of the electrode.

DETAILED DESCRIPTION OF THE PREFERRED EMBODIMENT

Figure 4:
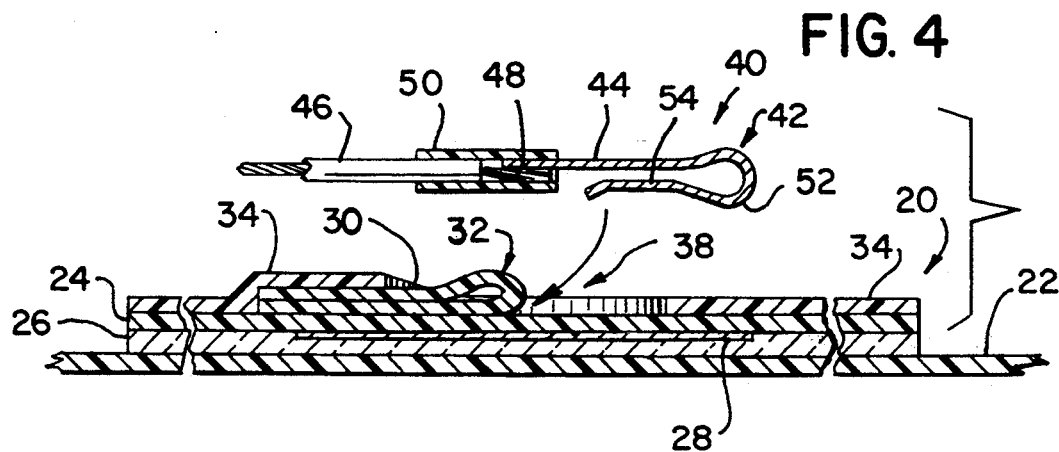
FIG. 4 is a cross-sectional view of the electrode of FIG. 3 along line 4—4 of that figure showing the electrode in assembled configuration.

Referring to FIGS. 2, 3 and 4, electrodes 20 of the present invention are arranged for use on a card 22 and held detachably to card 22 by a layer of hydrogel 26. The hydrogel 26 serves as both an adhesive and an electrolyte and may be any one of a commercially available hydrogel material used in the electrode industry. As used herein, hydrogel means generally a high water content gel produced by the coagulation of a colloid with the inclusion of water.

The hydrogel is selected to be lightly adherent, so as to retain the electrodes 20 on the card 22 or on the skin of the patient during use of the electrode 20, but sufficiently cohesive so that the electrode may be easily removed from the card 22 or skin without any residue of hydrogel 26 remaining on either.

As understood in the art, the conductivity of the hydrogel 26 is controlled by the addition of a nontoxic salt capable of ionization, such as sodium chloride, potassium chloride, sodium sulfate and others. The thickness of the hydrogel 26 is from approximately 5 to 50 mils and preferably from 25 to 30 mils, and preferably the volume resistivity of the hydrogel 26 should range from approximately $3 \times 10^4$ ohms-cm to approximately $4.5 \times 10^4$ ohms-cm. The preferable material of the hydrogel 26 is a 40% polyvinyl alcohol, however, other gel materials such as Karaya agar gum, alginates and the like could be used. Commercially available hydrogels are Lectec MP3000 and Medtronics Promeon.

The hydrogel 26 is applied to a "skin side" of a circular base sheet 24 of the electrode. The circular base sheet 24 is flexible and electrically conductive and may be constructed of a polyvinyl chloride film incorporating finely ground carbon particles, as is well understood in the art. Other means of producing conductive, flexible sheets, such as the deposition of a conductive layer on a non-conductive but flexible substrate could also be used. In the preferred embodiment, the conductive sheet is approximately 4 mils thick and has sufficient carbon to provide it with a surface resistance of 100 ohms-cm.

An electrochemically active material 28 is applied to a portion of the skin side of the circular base sheet 24 beneath the hydrogel 26. In the preferred embodiment, the electrochemically active material is a combination of silver and silver chloride such as is well known in the art for improving the electrical characteristics of medical electrodes.

The area of the skin side of the base sheet 24 over which the electrochemically active material 28 is applied depends on the particular use of the electrode. For stimulating electrodes subject to high polarizing currents, the entire skin side of the base sheet 24 may be coated with the electrochemically active material 28. For short term monitoring purposes, only a small area of the skin side of the base sheet is coated with electrochemically active material 28. This small area may be centered within the base sheet 24 or offset on the base sheet 24.

The electrochemical material 28 may be applied to the base sheet 24 in a number of ways well known in the art, including by a printing process or the pressing of silver and silver chloride onto the surface of the base sheet 24 or by plating or evaporating a layer of silver onto the base sheet and then reacting the silver with chlorine to produce the necessary silver chloride.

Attached to the circular base sheet 24, on the side opposite the skin side ("the lead side"), is a tab 30 formed of a strip of the same conductive material as comprises the circular base sheet 24. The tab 30 may also be coated with a surface metal layer. The material of the tab 30 is folded along its length to produce a folded edge 32 and the tab 30 is laid with this folded edge positioned diametrically along the circular base sheet 24.

An annular retaining sheet 34 having a central aperture 36 and a circumference substantially equal to that of the circular base sheet 24, is applied over the left and right opposing sides of the tab 30 (as viewed orientationally in FIG. 3) to sandwich the tab 30 between the lead side of the circular base sheet 24 and a lower surface of the annular retaining sheet 34. The lower surface of the annular retaining sheet 34 is coated with a pressure-sensitive adhesive to bond to the upper side of the tab 30 and importantly to bond the annular retaining sheet 34 to the portions of the lead side of the circular base sheet 24 exposed on either side of the tab 30.

The tab 30 and the central aperture 36 are positioned so as to expose the folded edge 32 of the tab 30 but so that the annular retaining sheet 34 covers all other edges of the tab 30 creating a pocket 38 and pressing the tab 30 against the circular base sheet 24 to provide good electrical contact between the tab 30 and the base sheet 24. The material of the annular retaining sheet 34 need not be conductive and in the preferred embodiment is a thin, printable, non-conductive polymer sheet.

As mentioned, the tab 30, as assembled against the circular base sheet 24, creates a narrow pocket 38 between the tab 30 and the lead side of the circular base sheet 24. The tab 30, forming one side of the pocket, is restrained generally along the plane of the circular base sheet 24. This pocket 38 receives connector 40 inserted along the plane of the circular base sheet 24 to provide electrical contact between the electrode 20 and that connector. The folded edge 32 of the tab 30 serves to create a raised lip on the pocket 38 guiding insertion of this connector. The aperture 36 of the annular retaining sheet 34 is sized so that the lip of the pocket formed by the folded edge 32 is substantially larger than the connector to permit insertion of the connector without the need for precise location of the connector with respect to the pocket 38.

Referring still to FIGS. 3 and 4, the connector 40 for use with the electrode 20 of the present invention includes a hook 42 formed, in the preferred embodiment, of a flat strip of phosphor-bronze plated with gold. The connector 40 has a generally straight shank portion 44 attached at its first end soldered to an exposed conductor 48 of a monitoring lead 46. Alternatively, it will be understood that mechanical crimping or bonding techniques may be used for this connection. The connection between the conductor of the monitoring lead 46 and the shank 44 is covered with an insulator 50 such as a heat shrinkable tubing or a molded covering.

The second end of the shank 44 forms a bend 52 to produce a bill 54 of the hook 42, the bill 54 returning substantially along the same direction as the shank 44 to create a gap between the shank 44 and the bill 54 substantially equal to the thickness of the tab 30. Thus, the free end of the bill 54 may be received within the pocket 38 formed by the tab 30 and the circular base sheet 24 with the shank 44 lying on the upper surface of the tab 30 and the monitoring lead 46, as covered by insulator 50, lying generally on top of the annular retaining sheet 34 and away from the patient's skin by virtue of the central location of the pocket 38.

The aperture 36 of the annular retaining sheet 34 is sized so that a sufficient portion of the tab 30 is exposed so that significant electrical conduction may be had both between the shank 44 and the tab 30, and between the bill 54 and the tab 30. The insertion of the bill 54 into the pocket 38 produces a wiping action, removing surface oxidation from the bill and insuring good conduction of low voltages between the electrode 20 and the monitoring lead 46. The action of the annular retaining sheet 34 holding the tab 30 against the lead side of the circular base sheet 24 preserves the low profile of the electrode 20 and connector 40 when the two are connected. The connector 40 may be plated with nickel or gold or other conductive materials.

Figure 5:
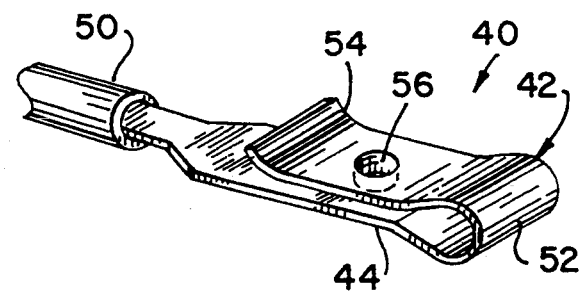
FIG. 5 is a perspective view of a first embodiment of the connector of FIGS. 1 and 3, inverted for clarity, showing the construction of a detent surface for resisting disengagement of the connector.

Referring now to FIG. 5, the bill 54 of the hook 42 may include a dimple 56 extending from the bill 54 toward the shank 44 creating between the dimple 56 and the shank 44, a detent surface spaced from the shank 44 by less than the thickness of the tab 30. Accordingly, when the bill 54 is inserted in the pocket 38, (not shown in FIG. 5), the detent surface presses against the tab 30 causing outward flexure of the bill 54 with respect to the shank 44 and causing a clamping of the tab 30 in the hook 42. This clamping improves electrical contact between the connector 40 and the electrode 20 and also helps the connector 40 resist from becoming dislodged from the tab 30 and electrode 20.

Figure 6:
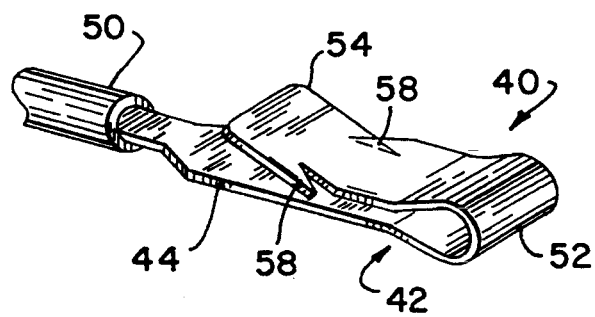
FIG. 6 is a figure similar to that of FIG. 5 showing a second embodiment of the connector of FIGS. 1 and 3 employing barbs which engage the material of the electrode to prevent disengagement of the connector of FIG. 6.

Alternatively, as shown in FIG. 6, barbs 58, extending into the pocket 38 from the hook 42, and opposed on either side the hook 42 along the axis of the lip 32, are pointed from the bill 54 toward the shank 44 and canted towards the bend 52. The barbs 58 allow insertion of the bill 54 into the pocket 38 with relatively little resistance but then prevent disengagement of the bill 54 from the pocket 38, in the manner of a barb on a fishhook, and prevent the connector 40 from being removed from the electrode 20 without destruction of the tab 30 and considerable force. The connector 40 of FIG. 6 would be used in situations where considerable activity of the patient would be expected.

Figure 7:
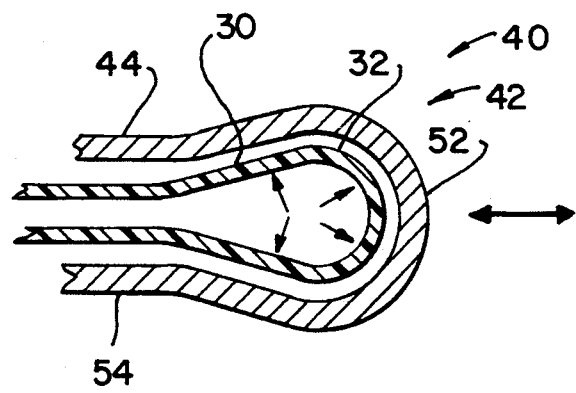
FIG. 7 is a detailed cross-sectional view along line 7—7 of FIG. 2 of the electrode engaged with the connector showing expansion of a lip of the pocket within a bend of the connector to provide positive engagement of the connector and pocket lip.

Referring to FIG. 7, the bend 52 of the hook 42 creates a cylindrical volume of slightly greater diameter than the average spacing between the bill 54 and the shank 44. This cylindrical volume permits expansion of the folded end 32 of the tab 30 into this volume once the connector 40 is fully engaged with the electrode 20.

The expansion of the folded edge 32 of the tab 30 is caused by the natural resilience of the material of the tab 30 and creates a "snap" effect providing tactile feedback indicating that a connection had been made. This expansion of the folded edge 32 also serves to retain the connector 40 on the tab 30.

Referring to FIG. 8, the electrode 20 is normally placed on the patient so that the dominant force on the monitoring lead 46 is along the insertion axis 62 generally lying along the axis of the shank 44 from the first to second end. Force along the insertion axis 62, in the insertion direction in which the bill 54 is placed within the pocket 38, serves generally to tighten the connection between the connector 40 and the electrode 20 compressing the bend 52 of the connector 40 against the folded edge 32 of the tab 30. At acute angles from the insertion axis 62, the connector 40 will attempt to shift within the pocket 38 so that the axis of the shank 44 attempts to align with the new perturbation force 60. Under such forces, the connector 40 will pivot about dimple 56 or one of the barbs 58 and the edge of bend 52 will deform the folded edge 32. The deformation of the folded edge 32 further retains the connector 40 against slippage. The use of the retaining sheet 34 to attach the tab 30 to the electrode 20 otherwise allows the connector 40 considerable freedom in rotating to accommodate forces placed on the monitoring leads 46.

Referring now to FIG. 9, the force along the insertion axis 62 opposite the direction of insertion, rather than causing the connector 40 to disconnect from the electrode 20 produces a camming action raising the first end of the shank 44 and forcing the bend 52 downward against the circular base sheet 24 resulting in an upward motion of the dimple 56 or barbs 58 against the lower surface of the tab 30 further resisting disengagement of the connector 40. The upward force of the bill 54 is largely centered within the electrode 20 and distributed over its adhesive area resisting any tendency of the electrode 20 to peel away from the skin of the patient. The central location of the central aperture 36 likewise causes the perturbing forces 60 discussed with respect to FIG. 8 to be distributed over a broad adhesive area resisting the tendency of the electrode 20 to peel away from the skin as may occur in electrodes where the attachment is near one edge of the electrodes adhesive surface.

Referring now to FIG. 10, in a second embodiment, the tab 30 may be formed from an unfolded sheet of conductive material similar to that of circular base sheet 24, laminated, as before, between the annular retaining sheet 34 and the circular base sheet 24. In this embodiment, the "snap" action or locating ridge of the folded edge 32 of FIG. 4 is not present. However, the low profile of the electrode 20 is preserved and the manufacturing process simplified.

As is also shown in FIG. 10, the hydrogel 26 may be located only on the portion of the skin side of the circular base sheet 24 over which the electrochemically active material 28 is placed. Outside of this area, an adhesive 70, having no conductive properties but having other desirable characteristics such as a stronger adhesive action, may be used. In this situation where separate adhesive 70 is employed, the hydrogel 26 may be replaced with a conventional electrolyte held in a foam pad or the like.

Referring to FIG. 11, conductivity between the tab 30 and the conductive base sheet 24 may be ensured by forming the tab 30 from a fold made in the material of the circular base sheet 24. Thus, it will be understood that the tab 30 need not be a separate piece of material but may be formed integrally with circular base sheet 24.

Many modifications and variations of the preferred embodiment which will still be within the spirit and scope of the invention will be apparent to those of ordinary skill in the art. In order to apprise the public of the various embodiments that may fall within the scope of the invention, the following claims are made:

I claim:

1. A medical electrode, providing electrical contact with the skin of a patient, comprising:
   a flexible conductive base sheet having a first side for placement next to the skin of the patient and a second side opposite to the first side;
   a flexible conductive tab having a top and bottom surface, and generally opposed left and right sides, the tab being conductively attached to the second side with the left and right sides attached to the second side to create between the second side and the bottom surface of the tab a pocket for the receipt of an electrical connector to establish electrical contact between the connector and the electrode.

2. The electrode of claim 1 wherein the pocket has a lip past which the electrical connector may be inserted and wherein the tab comprises a folded strip of flexible conductive material having a folded edge and wherein the folded edge forms the lip of the pocket.

3. The electrode of claim 1 wherein the tab is a folded portion of the base sheet.

4. The electrode of claim 1 including an electrochemically active material in electrical contact with the first side of the base sheet and adapted to be disposed between the skin and the base sheet for providing an electrical path between the skin and the base sheet.

5. The electrode of claim 4 wherein the electrochemically active material is a mixture of silver and silver chloride.

6. The electrode of claim 1 including an electrolyte applied to the first side of the base sheet and adapted to be disposed between the skin and the base sheet for providing an electrical path between the skin and the base sheet.

7. The electrode of claim 1 wherein a first portion of the first side of the base sheet is coated with an adhesive and a second portion of the first side of the base sheet is coated with an electrochemically active material, for providing an electrical path between the skin and the base sheet.

8. The electrode of claim 1 including an electrochemically active material in electrical contact with the first side of the base sheet, and adapted to be disposed between the skin and the base sheet for providing an electrical path between the skin and the base sheet, and including an electrolyte applied to the electrochemically active material, and adapted to be disposed between the skin and the electrochemically active material for providing an electrical path between the skin and the base sheet.

9. The electrode of claim 8 wherein the electrolyte is an adhesive.

10. The electrode of claim 1 wherein the pocket has a lip past which the electrical connector may be inserted and wherein the lip is substantially centered on the base sheet.

11. The electrode of claim 10 including in addition an annular retainer sheet having a central opening and attached to the second side of the base sheet and the top surface of the tab so that the central opening exposes a portion of the top surface of the tab including the lip.

* * * * *